United States Patent
Shuber et al.

(10) Patent No.: US 11,224,850 B2
(45) Date of Patent: Jan. 18, 2022

(54) REGULATED MULTIPLEX REACTIONS IN A SINGLE TUBE

(71) Applicant: GENETICS RESEARCH, LLC, Waltham, MA (US)

(72) Inventors: Anthony P. Shuber, Northbridge, MA (US); William Glover, Wakefield, MA (US)

(73) Assignee: GENETICS RESEARCH, LLC, Waltham, MA (US)

(*) Notice: Subject to any disclaimer, the term of this patent is extended or adjusted under 35 U.S.C. 154(b) by 0 days.

(21) Appl. No.: 16/795,970

(22) Filed: Feb. 20, 2020

(65) Prior Publication Data

US 2020/0261881 A1 Aug. 20, 2020

Related U.S. Application Data

(60) Provisional application No. 62/808,033, filed on Feb. 20, 2019.

(51) Int. Cl.
| | |
|---|---|
| C12Q 1/6806 | (2018.01) |
| C12Q 1/6876 | (2018.01) |
| B01J 19/00 | (2006.01) |
| C12N 15/11 | (2006.01) |
| C12N 9/22 | (2006.01) |
| C12Q 1/34 | (2006.01) |
| C12Q 1/48 | (2006.01) |
| C12Q 1/6848 | (2018.01) |
| C12N 9/06 | (2006.01) |
| C12N 15/113 | (2010.01) |

(52) U.S. Cl.
CPC ........ *B01J 19/0046* (2013.01); *C12N 9/0022* (2013.01); *C12N 9/22* (2013.01); *C12N 15/11* (2013.01); *C12N 15/113* (2013.01); *C12Q 1/34* (2013.01); *C12Q 1/48* (2013.01); *C12Q 1/6806* (2013.01); *C12Q 1/6848* (2013.01); *C12N 2310/20* (2017.05); *C12N 2800/80* (2013.01)

(58) Field of Classification Search
CPC ............. B01J 19/0046; C12N 2800/80; C12N 2310/20; C12Q 1/6806
See application file for complete search history.

(56) References Cited

U.S. PATENT DOCUMENTS

| | | |
|---|---|---|
| 5,985,619 A | 11/1999 | Sutherland et al. |
| 2015/0211058 A1 | 7/2015 | Carstens |
| 2015/0240280 A1 | 8/2015 | Gibson et al. |
| 2018/0154353 A1 | 6/2018 | Glezer et al. |
| 2018/0298421 A1 | 10/2018 | Carpenter et al. |
| 2018/0363042 A1 | 12/2018 | Solstad et al. |

OTHER PUBLICATIONS

Shin et al., CRISPR-Cas9-targeted fragmentation and selective sequencing enable massively parallel microsatellite analysis, Nature Communications, Feb. 7, 2017, 8(1):1-13.

*Primary Examiner* — Maryam Monshipouri
(74) *Attorney, Agent, or Firm* — Brown Rudnick LLP; Thomas C. Meyers

(57) ABSTRACT

The invention provided methods and devices for performing sequential, regulated multiplex reactions in a single tube without the addition or removal of contents from the tube.

10 Claims, 2 Drawing Sheets

REGULATED MULTIPLEX REACTIONS IN A SINGLE TUBE

CROSS-REFERENCE TO RELATED APPLICATION(S)

This application claims benefit of U.S. Provisional Application No. 62/808,033, filed Feb. 20, 2019, incorporated by reference.

TECHNICAL FIELD

The invention relates to methods and devices for performing sequential multiplex reactions in a single vessel.

BACKGROUND

A critical element to successful treatment of any illness or disease, whether it is a life-threatening type of cancer or the common cold, is early detection. Outcomes are better when treatment begins while the body is in good shape to combat the malady than when the body has become depleted while waiting for a diagnosis. In some cases, waiting for days to start treatment can determine whether the patient lives or dies.

Although recent biomedical advances have made it possible to identify and treat disorders that were previously intractable, the increased sophistication of diagnostic tests comes at a cost. As assays become more complex, they typically involve complicated series of manipulations that must be performed by skilled technicians. Specialized laboratory equipment may also be needed, so test samples may require processing at sites remote from the site of the interaction between the patient and health care professional, such as a physician or nurse. Consequently, patients often leave a visit to the doctor's office, health clinic, or other point of care without diagnoses, while their suffering continues and chances of receiving effective treatment wane as they wait for results.

SUMMARY

The invention provides methods and devices for performing a series of biochemical reactions sequentially in a single compartment. A sample to be analyzed is added to the compartment, which then is manipulated by, for example, changing the temperature, to cause reactions to proceed and/or stop. For example, a compartment, such as a tube, a micelle, an oil-in-water emulsion, or others as detailed below contains a sample and a series of enzymes that are activated by changing conditions surrounding the compartment, such as temperature. Alternatively or additionally, one may change the pH, salinity, or other physical chemical aspects in order to drive specific reactions, create an order of reactions, and/or stop reactions.

Methods and devices of the inventions allow complex analytical reactions to be performed on samples quickly and with minimal human intervention. As a result, methods and devices of the invention are useful for diagnostic assays that can be performed at the point of care. In addition, because the manipulations can be performed with compact equipment, the invention can be readily performed outside of a hospital setting. Thus, methods and devices of the invention allow patients to interact with physicians and other health professionals in remote or emergency settings and receive diagnostic results at the point of care within a very short turnaround time.

Aspects of the disclosure provide a reaction system that includes a reaction compartment comprising a first reaction component and a second reaction component, wherein the first and second reaction components may be independently activated and/or deactivated by a change to the compartment. The first and second reaction components may be independently activated or deactivated by a change to a temperature of the compartment. In some embodiments, the compartment comprises a sample tube. In certain embodiments, the first reaction component includes DNA-binding proteins and exonuclease and/or the second reaction component includes a thermostable polymerase. The first and second reaction components may be packaged together within a sample tube.

In some embodiments, when a sample comprising target nucleic acid and non-target nucleic acid is added to the reaction compartment and heated to the first temperature, the first reaction component digests the non-target nucleic acid, and when the reaction compartment is heated to a second temperature, the second reaction component synthesizes at least a portion of a copy of the target nucleic acid. Optionally, when a sample comprising target nucleic acid and non-target nucleic acid is added to the reaction compartment, the reaction compartment may be sealed and brought to a first temperature at which the first reaction component degrades the non-target nucleic acid and then the reaction compartment may—without unsealing the reaction compartment—be brought to a second temperature at which the section reaction component synthesizes a copy of a at least a portion of the target nucleic acid.

In certain embodiments the first reaction component comprises Cas endonuclease proteins, guide RNAs that target the Cas endonuclease proteins to target nucleic acids, and exonuclease; and/or the section reaction component comprises primers and thermostable DNA polymerase. Preferably the Cas endonuclease proteins are complexed with the guide RNAs as ribonucleoproteins and the primers include phosphorothioate linkages rendering the primers resistant to digestion by the exonuclease. The first reaction component and the section reaction component may be pre-packaged into the reaction compartment, and the reaction compartment is optionally a sample tube or well of a multi-well plate. It may be that a first physical chemical change to the compartment supports a first reaction but not a second reaction; and a second physical chemical change to the compartment supports the second reaction but not the first reaction.

In some embodiments: the a reaction compartment is provided as a sample tube or well of a multi-well plate containing therein the first and second reaction components, each present in the form of one or more beads or particles, wherein the first reaction component includes: at least one active or catalytically-inactive Cas endonuclease complexed with a guide RNA that targets the Cas endonuclease to a target nucleic acid, and exonuclease; and the second reaction component includes: at least one exonuclease resistant primer that hybridizes to the target nucleic acid and polymerase. Preferably, the first reaction component is active between about 30 and 45 degrees C. and the second reaction component is active between about 80 and 105 degrees C. The first and second reaction components may be present as lyophilized particles or hydrogel beads containing molecular reagents therein.

Aspects of the disclosure provide a sample preparation method that includes (i) obtaining a sample comprising a target nucleic acid; (ii) introducing the sample into a reaction compartment containing therein a first reaction component and a second reaction component; (iii) processing the target nucleic acid using the first reaction component; and (iv) causing a change to the compartment to thereby cause the second reaction component to process the target nucleic acid. The change to the compartment may include a change to a temperature of the compartment. The compartment may be a sample tube such as a microcentrifuge tube, blood collection tube, Falcon tube, or well of a multi-well plate. In some embodiments, the first reaction component includes DNA-binding proteins that bind to the target nucleic acid and exonuclease that digests non-target nucleic acid in the sample and/or the second reaction component includes a thermostable polymerase.

The method may include first heating the compartment to a first temperature to cause the first reaction component to digest non-target nucleic acid in the sample; and second heating the compartment to a second temperature to cause the second reaction component to synthesize at least a portion of a copy of the target nucleic acid. The method may include sealing the compartment prior to the heating steps.

In certain embodiments, the first reaction component comprises Cas endonuclease proteins, guide RNAs that target the Cas endonuclease proteins to target nucleic acids, and exonuclease; and/or the section reaction component comprises primers and thermostable DNA polymerase. The Cas endonuclease proteins may be complexed with the guide RNAs as ribonucleoproteins (RNPs) and the primers may include phosphorothioate linkages rendering the primers resistant to digestion by the exonuclease. In certain embodiments, the a reaction compartment is provided as a sample tube or well of a multi-well plate containing therein the first and second reaction components, each present in the form of one or more beads or particles, wherein the first reaction component includes: at least one active or catalytically-inactive Cas endonuclease complexed with a guide RNA that targets the Cas endonuclease to a target nucleic acid, and exonuclease; and the second reaction component includes: at least one exonuclease resistant primer that hybridizes to the target nucleic acid and polymerase. Optionally, the first reaction component is active between about 30 and 45 degrees C. and the second reaction component is active between about 80 and 105 degrees C. The first and second reaction components may be present has lyophilized particles or hydrogel beads containing molecular reagents therein.

In an aspect, the invention provides a reaction system containing more than two reactive components in a compartment in which the reactive components are activated and deactivated by a physical chemical change in the compartment without the addition or removal of reactants from the compartment. Preferably, the physical chemical changes are performed so that different reactive components are active at different times, and a series or reactions can be performed in sequence.

The series may include two or more reactions performed in sequence. For example, the series may include three, four, five, six, seven, eight, nine, ten, or more sequential reactions. The series may include steps that are performed sequentially, and steps may include individual reactions or multiple reactions performed concomitantly.

The reactive components may be any components capable of chemically reacting or catalyzing a chemical reaction. For example and without limitation, the reactive components may be enzymes, substrates, or cofactors.

The compartment may be any physical compartment suited to contain the reactive components. For example and without limitation, the compartment may be a vessel, vial, tube, vesicle, droplet, liposome, or the like.

The physical chemical change may be any change that alters the activity of at least one reactive component. For example, the physical chemical change may be a change in temperature, pH, concentration of a reagent in solution, solubility, binding of two or more reagents, electromagnetic radiation, light, sound, vibration, motion, pressure, or any combination thereof.

In an aspect, the invention provides methods of performing a series of steps sequentially in a reaction compartment comprising more than two reactive components by making physical chemical changes to the system without adding or removing reactants from the compartment.

DETAILED DESCRIPTION

Figure 1:
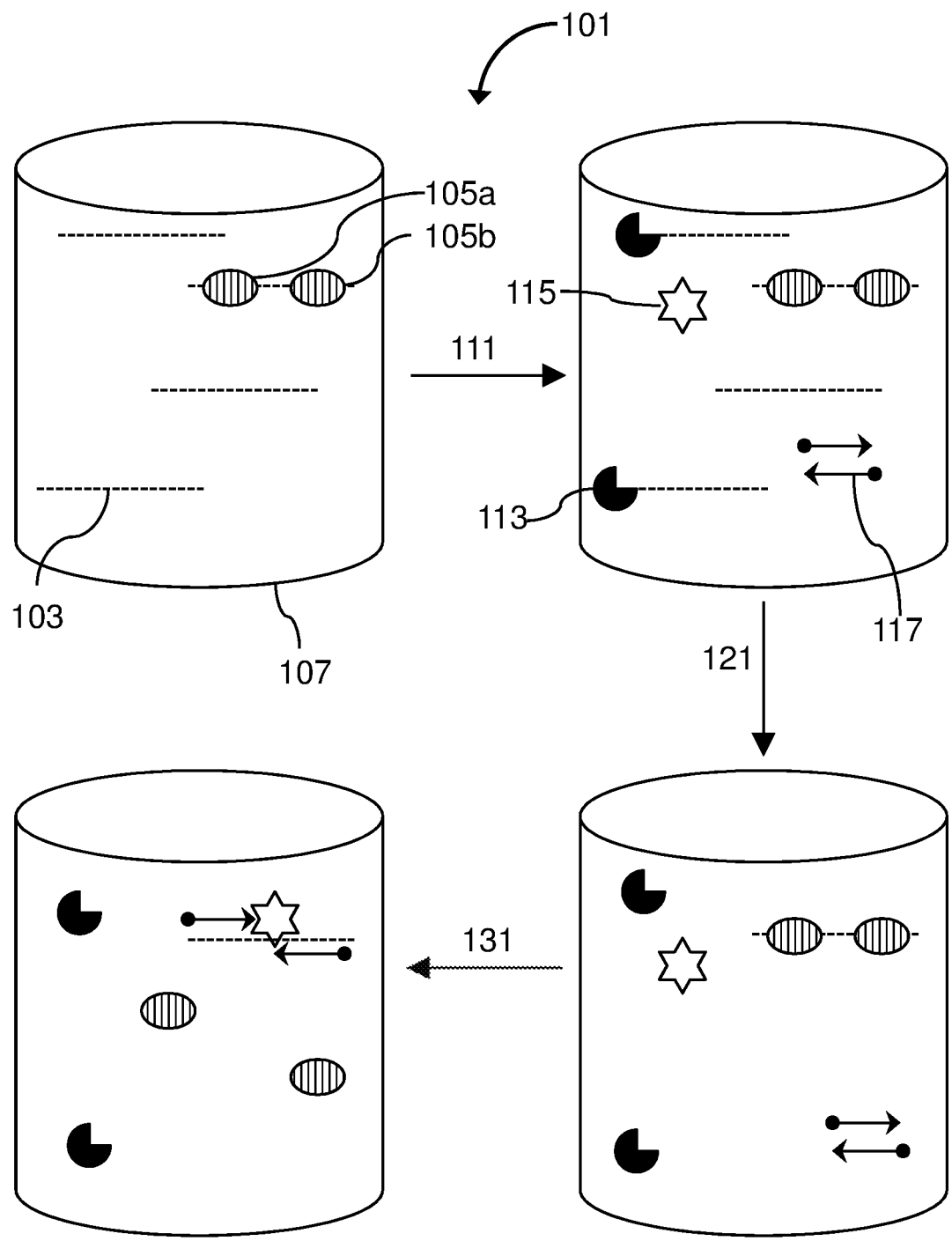
FIG. 1 illustrates a method according to an embodiment of the invention.

The invention provides methods of performing a series of steps sequentially in a reaction compartment comprising more than two reactive components by making physical chemical changes to the system without adding or removing reactants from the compartment. The steps may include enzymatic reactions. A step may include one or more than one enzymatic reaction.

The reactive components may be any components capable of chemically reacting or catalyzing a chemical reaction. For example and without limitation, the reactive components may be enzymes, substrates, or cofactors. Examples of enzymes include exonucleases, endonucleases, polymerases, ligases, and proteinases.

Thus, the invention provides methods in which multiple enzymes that are active under different conditions are combined in a compartment, such as a vessel, subject to a first set of conditions that permit a first reaction but not a second reaction to occur, and subject to a second set of conditions that prevent the first reaction but permit the second reaction to occur. Such a series may include any number of sequential reactions, for example, three, four, five, or more. Reactants and products are determined based upon the needs of the user.

The change in conditions may be physical chemical change. For example, the physical chemical change may be a change in temperature, pH, concentration of a reagent in solution, solubility, binding of two or more reagents, electromagnetic radiation, light, sound, vibration, motion, pressure, or a combination of any such changes. For example, a change in temperature may affect the solubility of a component in the compartment.

Enzymatic reactions may be regulated by a variety of mechanisms. For example, enzymes differ in temperatures at which they are active and temperatures at which they are unstable. It is therefore possible to perform a regulated sequence of enzymatic reactions by changing the temperature of the compartment. A first enzyme may be active at a low temperature but become denatured and inactivated at a high temperature, whereas a second enzyme may be inactive at the low temperature but active at the high temperature. Therefore, by incubating the reaction compartment first at the low temperature and subsequently at the high temperature, the reactions catalyzed by the first and second enzymes, respectively, can be performed in sequence.

Another mechanism for regulating enzymatic reactions is to control the physical interactions between enzymes, substrates, and cofactors. One way to regulate interactions is to use molecules that reversibly bind an enzyme, substrate, or cofactor. Examples of such molecules include aptamers, antibodies, chemical inhibitors (aka small molecule inhibitors), and reversible covalent cross-linkers. Thus, an enzyme may be added to the compartment initially in a complex with another molecule that prevents the activity of the enzyme, and a subsequent change in the conditions disrupts binding between the enzyme and the binding partner, allowing the enzyme to perform its catalytic function. A similar approach may be used with a substrate or cofactor.

Enzymes can also be regulated by providing them in a reversibly encapsulated form that prevents the enzyme from interacting with substrates or cofactors. Examples of encapsulation forms include liposomes, vesicles, polymersomes, micelles, emulsions, temperature-sensitive capsules, hydrogels, sol-gels, other organic-inorganic hybrid materials, and layer-by-layer structures made through controlled assembly of polyelectrolytes. Encapsulated forms may have one or multiple layers, and the layers may have the same or different chemical compositions. Microencapsulation of enzymes is described in Rother, 2014, Enzyme Immobilization by Microencapsulation: Methods, Materials, and Technological Applications (2014), DOI: 10.1002/9780470054581; Sakr, 2013, Encapsulation of Enzymes in Layer-by-Layer (LbL) Structures: Latest Advances and Applications, Biomacromolecules 14(7):2117-2135; Besic, 2011, Micellar polymer encapsulation of enzymes, Methods Mol Biol 679:113-31; Gan, 2012, Temperature-Triggered Enzyme Immobilization and Release Based on Cross-Linked Gelatin Nanoparticles, PLoS One 7(10):e47154, all incorporated by reference. Similar strategies can be used to encapsulated substrates or cofactors for enzymes.

Enzyme activity can also be regulated by removing an enzyme from solution via precipitation. For example, an enzyme may be bound to a binding moiety conjugated to an insoluble particle to remove the enzyme from solution. The binding moiety may be an antibody. The particle may be any type of particle that can be separated from a suspension. The particle may be a magnetic particle.

Enzyme activity can be regulated by removing a cofactor or substrate from solution via precipitation. For example, many enzymes require $Mg(2+)$ as a cofactor, and $Mg(2+)$ can be precipitated by exposure to phosphate ions. Thus, the compartment may include phosphate ions that are released to cause precipitation of $Mg(2+)$ and terminate an enzymatic reaction.

Another way to regulate enzyme activity is to change pH. Enzymes vary in their optimal pH for activity, so a change in pH may inactivate a first enzyme and activate a second enzyme. Thus, an acid or base may be release within the compartment to change the pH of the solution within the compartment and initiate a transition from one reaction to another. Nitric acid (HNO3) reduces pH and decomposes to water and inert gases when heated, so it can be used without permanently disrupting subsequent reactions. Similarly, HCl reduces pH and can be neutralized with NaOH to create NaCl.

Enzyme activity can also be regulated by the use of redox reagents. For example, hydrogen peroxide causes oxidative damage that can terminate activity of an enzyme. However, it decomposes upon heating, so it can be used without permanently disrupting subsequent reactions.

In some embodiments, the methods include providing enzymes or other reagent encapsulated in a multilayered capsule in which a different set of enzymes or reagents is contained within each layer. The capsule is designed so that individual layers and their components are released at each change of conditions, for example, in one change in temperature or thermal cycle between two temperatures. Consequently, after one thermal cycle, a first set of reagents is released, and a first reaction is performed; after a second thermal cycle, a second set of reagents is released, and a second reaction is performed; etc.

The methods may be performed with any enzyme. Enzymes that alter the structure or function of proteins and nucleic acids are particularly useful for diagnostic assays. Thus, the methods may include exonucleases, endonucleases, polymerases, ligases, or proteinases.

The compartment may be any physical compartment suited to contain the reactive components. The compartment may be a vessel, vial, tube or other similar object than can be directly handled, e.g., held in the hand. Alternatively, the compartment may a fluid compartment, such as a vesicle, droplet, liposome, or the like.

The compartment may contain subcompartments that hold a subset of the reagents in the compartment. The subcompartments may keep some of the reagents separate from others for one or more reactions or steps in the series. The subcompartments may be destructible, and destruction of the subcompartments may release reagents into the greater compartment. The subcompartments may be destroyed by any physical chemical change described above, such as a change in temperature, pH, concentration of a reagent in solution, solubility, binding of two or more reagents, electromagnetic radiation, light, sound, vibration, motion, pressure, or any combination thereof.

The methods may include a series of steps, which may include enzymatic reactions. A step may include one or more than one enzymatic reaction. For example, a step in a method may include two enzymatic reactions that occur concomitantly. Alternatively, a step may comprise a single reaction.

The steps may differ in the types of reaction that occur during the steps. For example, a step may include only reactions that modify nucleic acids, only reactions the modify proteins, or both reactions that modify nucleic acids and proteins. Thus, by ordering the steps, it is possible to perform a step that includes one or more reactions using nucleic acids as substrates but no reactions using proteins as substrate, followed by a step that includes one or more reactions that use proteins as substrates but reactions using nucleic acids as substrates. Any sequence of steps is possible, such as a protein reaction followed by a DNA reaction, a DNA reaction followed by a protein reaction, etc. Examples of nucleic acid reactions include exonuclease digestion, endonuclease digestion, chain elongation, ligation, end modification (e.g., phosphorylation, dephosphorylation), gap repair, nicking, methylation, demethylation, and the like. Example of protein reactions include proteolytic cleavage, phosphorylation, amino acid side chain modification (e.g., phosphorylation, glycosylation), lipid addition, lipid removal, terminal modification, and the like.

The compartment may contain a sample or portion of a sample. For example, the compartment may contain a body fluid sample. The body fluid may be blood, plasma, serum, urine, sputum, phlegm, saliva, feces, semen, or any other body fluid.

The compartment may contain a substrate from a sample. For example, the compartment may contain a nucleic acid, e.g., DNA or RNA, protein, antibody, carbohydrate, lipid, or other biological macromolecule.

The reactive components may be any components capable of chemically reacting or catalyzing a chemical reaction. For example and without limitation, the reactive components may be enzymes, substrates, or cofactors. Examples of enzymes include exonucleases, endonucleases, polymerases, ligases, and proteinases.

In some embodiments, methods of the invention involve identification of specific nucleic species within a mixture of nucleic acids. Such methods may include a negative enrichment step to remove most or all of the non-target nucleic acids. Negative enrichment of nucleic acids is described, for example, in U.S. Pat. Nos. 10,527,608 and 10,081,829, both incorporated by reference.

This disclosure recognizes a useful objective in diagnostics to develop tests that can be performed with a very short turnaround time (TAT) and a result being generated at or very near the location of the patient/physician interaction (Point of Care, POC). POC testing leads to early intervention and in many cases improved therapeutic response.

Point-of-care tests of the disclosure use different enzymes whose reactions previously had to be done in separate reaction vesicles because the enzymes involved are incompatible based on reaction buffer conditions or even worse, incompatible enzymatic properties (e.g. Exonucleases vs. polymerases).

This disclosure provides novel approaches to significantly reduce the complexity of molecular diagnostics analysis to provide for more complex molecular diagnostic assays to be offered within POC (Point of Care) tests or settings. The invention involves combining all components and enzymes in a single reaction vesicle that would normally be separated into two separate tubes. The differentiating variable is that the enzymes of interest are chosen or engineered to have different temperatures for activity such that the test tube containing the mixture of components is incubated at the lower temperatures initially, and the sample is exposed to an increase in temperature which would activate other enzymes that have higher activity temperatures.

In one embodiment, the invention is directly applied to one technology (Negative Enrichment) which involves binding the Cas9/gRNA complexes at a low temperature (e.g. 37 degrees C.) followed by the addition of exonucleases and PCR primers that have phophorothioated bases incorporated into their sequences, as well as thermal stable Taq polymerase (e.g. Hotstart Taq). The Polymerase is inactive at the lower temp. (37 degrees C.) where the activity of the exonuclease is optimal. In addition, the incorporation of phosphorothioated bases into the PCR primers make the primers resistant to exonuclease digestion. Following exonuclease digestion of regions of DNA that are not protected by the Cas9/gRNA complex at 37 degrees C., the temperature is raised to 95 degrees C. for some time that heat inactivates the exonuclease and activates the polymerase for amplification of target sequences within the Cas9/gRNA protected region.

In a second embodiment, the invention involves choosing and mixing different enzymes that have different temperatures for enzymatic activity and mixing them in a single tube. The single tube multiplex reactions are then carried out by starting at the lowest temperature associated with a specific reaction followed by an increase in temperature to different temperatures associated with optimal activities of the different enzymes. An important consideration of this approach is to make sure that the series of temperature/enzyme combinations is consistent with the series of experimental steps that would be performed in separate reaction tubes.

In another embodiment, a series of reagents are developed that have different temperatures associated with the solubility properties of each reagent. This approach addresses the issue that many enzymes have the same temperatures of activity and heat inactivation. When a single tube multiplex reaction is needed, the different temperature associated reaction components are mixed with the different enzymes based on the series of experimental reactions planned. This approach would eliminate the need to identify specific enzymes that inherently having different activity temperatures. However, one issue that still exists is the probable need to inactivate enzymes from earlier reaction steps. To address this need, within each reagent mix that has a specific temperature associated solubility factor, Abs, epitope specific, or enzyme specific inhibitors are added to later enzyme/reagent mixes that specifically inhibit enzymes used in earlier steps. This approach eliminates the need to inhibit earlier reaction steps with heat only. The "reagents" referred to in this last embodiment of the invention can be made up of anything that has the properties of solubility needed for the intended purpose. Examples of such reagents may be beads or micelle like structures where enzymes and components for different reactions are contained within them that get released once the temperature dependent reagents dissolve at their specific and intended temperature.

It should be noted that it will be clear to one skilled in the art that there are many different reagents or combination of reagents that can be used or synthesized to achieve the intended objective of creating a temperature depended single tube multiplex reaction.

EXAMPLES

Example 1

FIG. 1 illustrates a method 101 according to an embodiment of the invention. In the method 101, a negative enrichment is first performed. Genomic DNA 103 and two Cas9-gRNA complexes 105a, 105b specific for target sequences that flank a region of interest within the genomic DNA 103 are added to a vessel 107, which is incubated at 37 degree C. to allow the Cas9-gRNA complexes 105a, 105b to bind to their targets and protect species of genomic DNA 103.

Next, exonucleases 113, a heat-activated polymerase 115, and phosphorothioated PCR primers 117 for the target are added 111 to the vessel 107. The vessel 107 is incubated 121 at 37 degree C. to allow the exonucleases 113 to digest unprotected genomic DNA 103. The PCR primers 117 are not digested due to the phosphorothioate linkages.

The vessel 107 is then heated 131 to 94 degrees C., which inactivates the exonucleases 113, activates the thermostable polymerase, releases the Cas9-gRNA complexes 105a, 105b from their targets, and allows the DNA to denature. PCR is performed using standard thermal cycling to amplify target DNA.

Steps of the method of Example 1 is provided in the Table 1.

TABLE 1

Example 1, Cas9/Exonuclease Mediated gDNA Negative Enrichment, with PCR for NGS

| Process Step | Change of conditions | Change of Reactivity | Reaction |
|---|---|---|---|
| Reagents Added to Tube<br>Genomic DNA<br>Two Cas9/gRNA complexes | | None | None |
| Incubation Time | Incubate at 37 C. | None | Cas9/gRNA complexes bind to select loci, flanking region of gDNA to be protected. |
| Reagents Added to Tube<br>Exonuclease cocktail<br>Heat-activated polymerase (eg Hot Start Taq)<br>Phosphorothioated PCR primers | | None | None |
| Incubation Time | Incubate at 37 C. | None | gDNA digested by exonuclease cocktail, except for locus flanked by CAS9/gRNA complexes. Phosphorothioated primers not digested by exonucleases which are inhibited by phosphorothioated bases |
| Inactivate Exonucleases & Activate Polymerase | Heat to 94 C., then cool | Exonucleases thermally denatured Polymerase thermally activated | None |
| PCR | Thermal Cycling | None | PCR |

Example 2

Figure 2:
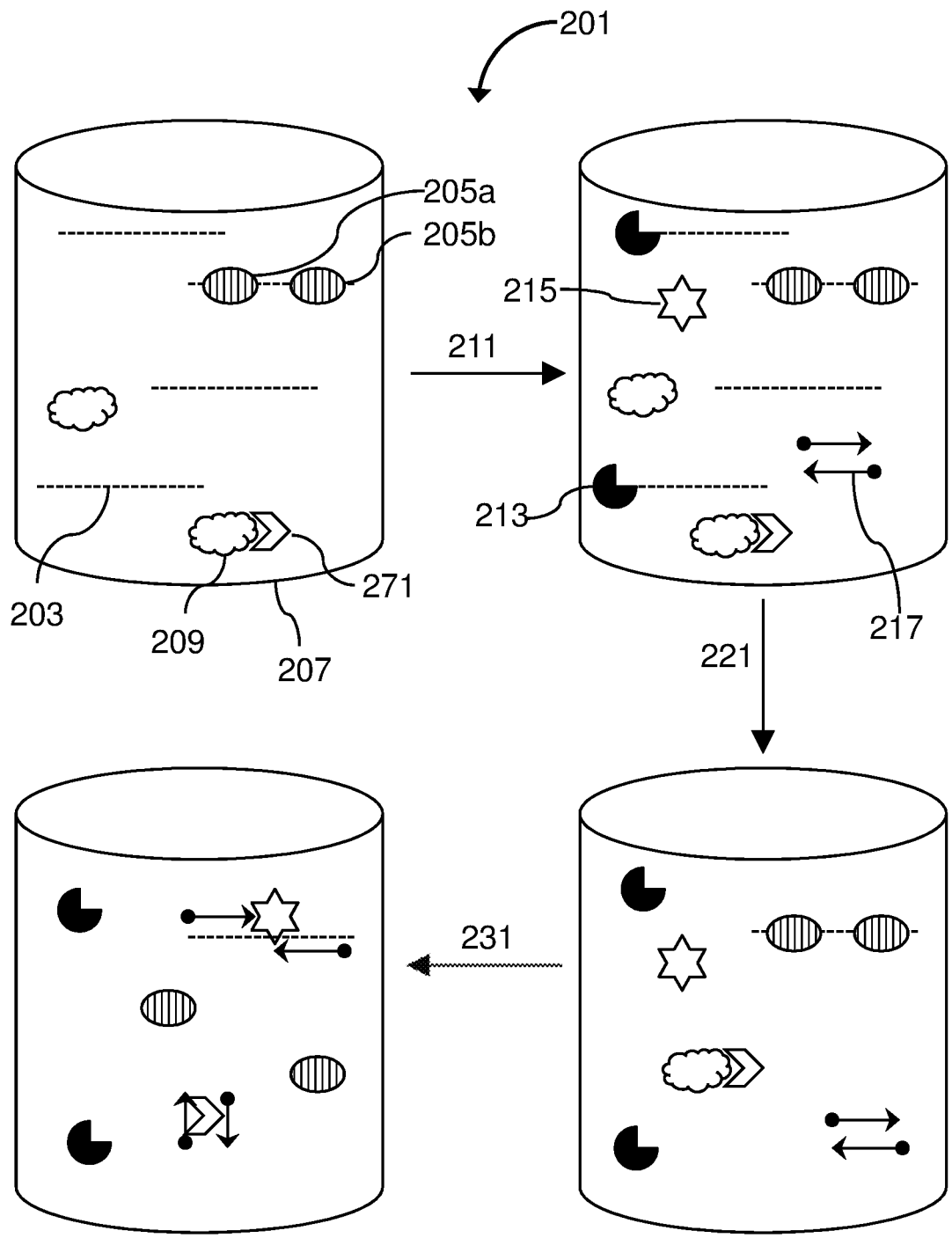
FIG. 2 illustrates a method according to an embodiment of the invention.

FIG. 2 illustrates a method 201 according to an embodiment of the invention.

In the method 201, a negative enrichment is performed by adding to a vessel 207 a sample containing genomic DNA 203 and proteins 209, two Cas9-gRNA complexes 205a, 205b specific for target sequences that flank a region of interest within the genomic DNA 203, and an oligonucleotide aptamer 271 unique to an epitope of interest. The vessel is incubated at 37 degrees C. to allow the Cas9-gRNA complexes to bind to their targets and protect species of genomic DNA.

Next, exonucleases 213, a heat-activated polymerase 215, and phosphorothioated PCR primers 217 for a genomic DNA locus, and phosphorothioated PCR primers 217 for the aptamer and target are added 211 to the vessel 207. The vessel 207 is incubated 221 at 37 degrees C. to allow the exonucleases to digest unprotected genomic DNA 203 and any aptamers 271 that are not bound their target epitopes.

The vessel is then heated 231 to 94 degrees C., which inactivates the exonucleases 213, activates the thermostable polymerase 215, releases the Cas9-gRNA complexes 205a, 205b from their targets, disassociates the aptamers 271 from their target epitopes, and allows the DNA to denature. PCR is performed using standard thermal cycling to amplify target DNA.

A flow chart for the method of Example 2 is provided in the Table 2.

TABLE 2

Example 2, Multi-Omics: Cas9/Exonuclease Mediated Protein Identification, gDNA Negative Enrichment and PCR for NGS

| Process Step | Change of conditions | Change of Reactivity | Reaction |
|---|---|---|---|
| Reagents Added to Tube<br>Genomic DNA & proteins<br>Two Cas9/gRNA complexes<br>Oligonucleotide aptamer unique to epitope of interest | | None | None |
| Incubation Time | Incubate at 37 C. | None | 1. Cas9/gRNA complexes bind to select loci, flanking region of gDNA to be protected. |

TABLE 2-continued

Example 2, Multi-Omics: Cas9/Exonuclease Mediated Protein Identification, gDNA Negative Enrichment and PCR for NGS

| Process Step | Change of conditions | Change of Reactivity | Reaction |
|---|---|---|---|
| | | | 2. Aptamer binds to target protein, if and only if such protein is present. |
| Reagents Added to Tube Exonuclease cocktail Heat-activated polymerase (e.g. Hot Start Taq) Phosphorothioated PCR primers for DNA locus Phosphorothioated PCR primers for aptamer | | None | None |
| Incubation Time | Incubate at 37 C. | None | gDNA digested by exonuclease cocktail, except for locus flanked by CAS9/gRNA complexes. Phosphorothioated primers not digested by exonucleases which are inhibited by phosphorothioated bases. Aptamers digested, except for population which has bound specifically to protein of interest. |
| Inactivate Exonucleases & Activate Polymerase | Heat to 94 C., then cool | Exonucleases thermally denatured Cas9/gRNA complexes thermally separated from DNA. Cas9 proteins thermally denatured Aptamers disassociated from proteins of interest | None |
| PCR | Thermal Cycling | None | Multi-omic NGS sample: DNA region of interest amplified, with NGS-compatible primers Aptamers amplified with NGS-compatible primers |

Example 3

In another example, a sample containing genomic DNA, double-stranded DNA adapters, a low-temperature fragmentation enzyme, medium-temperature end repair enzymes, a high-temperature DNA ligase, and a thermostable polymerase are added to a vessel. The vessel is incubated at 20 degrees C. to allow the fragmentation enzyme to cleave the genomic DNA, while the other enzymes remain inactive.

The vessel is then incubated at 37 degrees C. to inactivate the fragmentation enzyme and activate the end repair enzymes. The high temperature DNA ligase and thermostable polymerase 315 remain inactive during this step.

The vessel in then incubated at 65 degrees C. to inactivate the end repair enzymes and activate the high-temperature ligase.

Next, the vessel is incubated 341 at 94 degrees C. to inactivate the high-temperature ligase, activate the thermostable polymerase, and denature DNA. PCR is performed using standard thermal cycling to amplify DNA.

A flow chart for the method of Example 3 is provided in the Table 3.

TABLE 3

Example 3, Rising Temperature for Sequential Reactions: NGS Sample Prep

| Process Step | Change of conditions | Change of Reactivity | Reaction |
|---|---|---|---|
| Reagents Added to Tube gDNA dsDNA adapters Low Temperature fragmentation | | None | None |

TABLE 3-continued

Example 3, Rising Temperature for Sequential Reactions: NGS Sample Prep

| Process Step | Change of conditions | Change of Reactivity | Reaction |
|---|---|---|---|
| enzyme Medium Temperature end repair enzymes High Temperature dsDNA Ligase Hot Start Polymerase & Primers | | | |
| Fragment | Incubate at 20 C. | Low Temp fragmentation enzyme is active Medium Temp and High Temp enzymes are inactive | gDNA fragmented by Low Temp fragmentation enzyme |
| Repair | Incubate at 37 C. | Medium Temp Enzyme is activated (e.g. release of inactivating aptamer) Low Temp fragmentation enzyme is denatured High Temp Ligase remains inactive | DNA end repair |
| Ligate | Incubate at 65 C. | High Temp Ligase is activated (eg release of inactivating aptamer) Medium Temp enzyme is denatured | Adapters ligated to DNA |
| Activate Polymerase | Heat to 94 C., then cool | Hot Start Polymerase Activated | None |
| PCR | Thermal Cycling | None | PCR |

Example 4

In another example, a negative enrichment is performed by adding to a vessel a sample containing genomic DNA, two Cas9-gRNA complexes specific for target sequences that flank a region of interest within the genomic DNA, a cocktail of exonucleases micro-encapsulated in a thin layer, and a proteinase microencapsulated by a thick layer. The vessel is incubated to allow the Cas9-gRNA complexes bind their targets.

The vessel is then heated and cooled to allow the exonucleases to be released from their encapsulated form and digest unprotected genomic DNA. The layer surrounding the micro-encapsulated proteinases is reduced but not eliminated during this step, so the proteinases are not active during this step.

The vessel is then heated and cooled again to allowing removal of the remaining layer surrounding the proteinases. The proteinases are allowed access to substrates and degrade the exonucleases and other proteins to end all enzymatic reactions.

A flow chart for the method of Example 4 is provided in the Table 4.

TABLE 4

Example 4, Cas9/Exonuclease Mediated gDNA Negative Enrichment

| Process Step | Change of conditions | Change of Reactivity | Reaction |
|---|---|---|---|
| Reagents Added to Tube: Genomic DNA Two Cas9/gRNA complexes Micro-encapsulated exonuclease cocktail, thin layer Micro-encapsulated Proteinase, thick layer | | None | None |
| Incubation Time | | None | Cas9/gRNA complexes bind to select loci, flanking region of gDNA to be protected. |

TABLE 4-continued

Example 4, Cas9/Exonuclease Mediated gDNA Negative Enrichment

| Process Step | Change of conditions | Change of Reactivity | Reaction |
|---|---|---|---|
| Release of Exonuclease | Heat, then cool | 1. Micro-encapsulated exonucleases released<br>2. Micro-encapsulated proteinase layer reduced, but not eliminated | None |
| Incubation Time | | None | gDNA digested by exonuclease cocktail, except for locus flanked by CAS9/gRNA complexes |
| Release of Proteinase | Heat, then cool | Micro-encapsulated proteinase released | None |
| Incubation Time | | None | Exonucleases and Proteinases degraded. All reactions ended. |

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

What is claimed is:

1. A reaction system comprising:
   a single reaction compartment comprising:
   a first set of reaction components comprising Cas endonuclease proteins and guide RNAs that together form a complex that target sequences that flank a target nucleic acid, thereby protecting the target nucleic acid, if present in the compartment, from exonuclease digestion and an exonuclease,
   wherein the first set of reaction components are active at a first temperature and inactive at a second higher temperature; and
   a second set of reaction components comprising primers and a thermostable polymerase active at the second temperature and inactive at the first temperature, wherein the first and second set of reaction components may be independently activated and/or deactivated by a change in the temperature of the compartment.

2. The system of claim 1, wherein the compartment comprises a sample tube.

3. The system of claim 1, wherein the first and second set of reaction components are packaged together within a sample tube.

4. The system of claim 1, wherein when a sample comprising target nucleic acid and non-target nucleic acid is added to the reaction compartment and heated to the first temperature, the first set of reaction components digests the non-target nucleic acid, and when the reaction compartment is heated to a second temperature, the second set of reaction components synthesizes a copy of the target nucleic acid.

5. The system of claim 1, wherein, when a sample comprising target nucleic acid and non-target nucleic acid is added to the reaction compartment, the reaction compartment may be sealed and brought to a first temperature at which the first set of reaction components degrades the non-target nucleic acid and protects the target nucleic acid and then the reaction compartment may, without unsealing the reaction compartment, be brought to a second temperature at which the second set of reaction components synthesizes a copy of the target nucleic acid.

6. The system of claim 1, wherein the Cas endonuclease proteins are complexed with the guide RNAs as ribonucleoproteins and the primers include phosphorothioate linkages rendering the primers resistant to digestion by the exonuclease.

7. The system of claim 1, wherein the first set of reaction components and the second set of reaction components are pre-packaged into the reaction compartment, and the reaction compartment is a sample tube or a well of a multi-well plate.

8. The system of claim 1, wherein the reaction compartment is provided as a sample tube or a well of a multi-well plate containing therein the first and second set of reaction components, each present in the form of one or more beads or particles, wherein the first set of reaction components includes: at least one active or catalytically-inactive Cas endonuclease complexed with a guide RNA that targets the Cas endonuclease to sequences that flank a target nucleic acid, and exonuclease; and the second set of reaction components includes:
   at least one exonuclease resistant primer that hybridizes to the target nucleic acid and polymerase.

9. The system of claim 8, wherein the first set of reaction components is active between about 30 and 45 degrees C. and the second set of reaction components is active between about 80 and 105 degrees C.

10. The system of claim 8, wherein the first and second set of reaction components are present as lyophilized particles or provided by hydrogel beads.

* * * * *